United States Patent [19]
Hiraoka et al.

[11] Patent Number: 5,298,065
[45] Date of Patent: Mar. 29, 1994

[54] ULTRAVIOLET-SCREENING SCALE PIGMENT, PROCESS FOR PREPARING THE PIGMENT AND COSMETICS CONTAINING THE PIGMENT

[75] Inventors: Nobumoto Hiraoka; Norihiro Tanimoto; Mayumi Mandai, all of Okayama, Japan

[73] Assignee: Tayca Corporation, Osaka, Japan

[21] Appl. No.: 218

[22] Filed: Jan. 4, 1993

[30] Foreign Application Priority Data

Mar. 5, 1992 [JP] Japan .................................. 4-84557

[51] Int. Cl.$^5$ .......................... C04B 14/20; C08J 7/04; A61K 7/42
[52] U.S. Cl. ..................... 106/425; 106/415; 106/416; 106/426; 427/218; 427/372.2; 424/59
[58] Field of Search ............... 106/415, 417, 425, 426; 427/215, 218, 372.2; 424/59

[56] References Cited

U.S. PATENT DOCUMENTS

| | | | |
|---|---|---|---|
| 3,028,250 | 4/1962 | Dunn, Jr. ................ | 106/426 |
| 3,072,495 | 1/1963 | Pitrot ..................... | 106/426 |
| 4,207,377 | 6/1980 | Kindrick ................. | 106/426 |
| 4,331,706 | 5/1982 | Kindrick ................. | 106/425 |
| 4,781,982 | 11/1988 | Musselman et al. ....... | 106/417 |
| 4,956,019 | 9/1990 | Noguchi et al. .......... | 106/425 |
| 5,126,204 | 6/1992 | Tono et al. .............. | 427/215 |

FOREIGN PATENT DOCUMENTS

| | | |
|---|---|---|
| 0256417 | 2/1988 | European Pat. Off. . . |
| 1326901 | 4/1963 | France . |
| 49-450 | 1/1974 | Japan . |
| 61-257909 | 11/1986 | Japan . |
| 62-16408 | 1/1987 | Japan . |
| 62-228006 | 10/1987 | Japan . |

OTHER PUBLICATIONS

Patent Abstracts of Japan, vol. 15, No. 431 (C-881), Nov. 5, 1991, JP-A-31 81 411, Aug. 7, 1991.
Database WPI, Derwent Publications Ltd., Class D21, AN 93-71009, JP-A-5 017 329, Jan. 26, 1993.
Chemical Abstracts, vol. 100, No. 22, May 28, 1984, AN 177278f, "Nacreous Silver Pigment with a Rutile Structure", Miroslav Nedorost, et al., p. 137.

*Primary Examiner*—Helene Klemanski
*Attorney, Agent, or Firm*—Oblon, Spivak, McClelland, Maier & Neustadt

[57] ABSTRACT

Disclosed herein are an ultraviolet-screening scale pigment comprising scale-like inorganic particles and a zinc oxide coating layer of 50 to 250 wt% (calculated as ZnO) based on the scale-like inorganic particles, a water content of said zinc oxide coating layer being not more than 7 wt%; a process for producing the scale pigment; and cosmetics containing the scale pigment.

22 Claims, 2 Drawing Sheets

ULTRAVIOLET-SCREENING SCALE PIGMENT, PROCESS FOR PREPARING THE PIGMENT AND COSMETICS CONTAINING THE PIGMENT

BACKGROUND OF THE INVENTION

The present invention relates to an ultraviolet-screening scale (flake) pigment comprising scale-like (flaky) inorganic particles having their surfaces coated with a zinc oxide, a process for preparing such pigment, and cosmetics containing such pigment.

The ultraviolet rays existing in nature are roughly divided into two types according to wavelength. One is called UV-A having wavelengths ranging from 320 to 400 nm and the other is UV-B having wavelengths less than 320 nm. It is said that UV-A, when applied to the human skin, causes pigmentation, while UV-B is causative of suntan (see, for example, "Shikizai (Toner)", 63 (3), 171-175, 1990).

The pigments used for the anti-suntan cosmetics are required to have an ability to effectively screen the ultraviolet rays. Many studies have been made on this subject, and various ultraviolet-screening pigments have been proposed.

For instance, Japanese Patent Application Laid-Open (Kokai) No. 49-450 (1974) proposes an ultraviolet-protecting cosmetic composition containing fine titanium dioxide particles.

Also, Japanese Patent Application Laid-Open (Kokai) No. 62-228006 (1987) proposes fine zinc oxide particles as a substance which can effectively screen UV-A having wavelengths around 360 nm.

Further, Japanese Patent Application Laid-Open (Kokai) No. 61-257909 (1986) proposes cosmetics containing particles having a specific surface area of 15 to 100 m$^2$/g and coated with zinc white and/or zinc carbonate, and Japanese Patent Application Laid-Open (Kokai) No. 62-16408 (1987) discloses hiding cosmetics blended with mica particles having their entire surfaces coated uniformly with one or more of metallic oxides or metallic hydroxides such as oxides or hydroxides of titanium, zinc or ferrite to a thickness of 5 to 30 nm.

Fine titanium dioxide particles have an ultraviolet screening effect, but their screening effect is low against the ultraviolet rays with wavelengths of not less than 350 nm which falls within the wavelength region of UV-A.

Also, fine zinc oxide particles, which have been reported to be capable of effectively screening UV-A with wavelengths around 360 nm, are poor in dispersibility when blended in cosmetics and also costly.

Further, in the case of the inorganic particles coated with a zinc-based substance, disclosed in Japanese Patent Application Laid-Open (Kokai) No. 61-257909 (1986), since the zinc-based substance is merely deposited on the surfaces of the inorganic particles by dry-mixing, the substance is not uniformly coated on the surfaces of the inorganic particles, therefore the screening effect thereof against UV-A is not satisfactory.

In the case of mica coated with an oxide of a metal such as zinc, disclosed in Japanese Patent Application Laid-Open (Kokai) No. 62-16408 (1987), the object thereof is to improve the surface properties of mica, and the coating amount of the metallic oxide is too small to provide a sufficient screening effect against UV-A.

As viewed above, any of the hitherto proposed ultraviolet-screening pigments had some disadvantages such as unsatisfactory screening effect against ultraviolet rays, poor dispersibility, etc.

Thus, an offer of a pigment for cosmetics which has an excellent ultraviolet-screening effect, especially high screening effect against UV-A and a good dispersibility in cosmetic compositions, is demanded.

As a result of the present inventors' studies, it has been found that by suspending scale-like inorganic particles in water, adding an aqueous solution of a water-soluble zinc compound into the suspension, adjusting the pH of the resulting suspension to 9 to 11, hydrolyzing the zinc compound while gradually lowering the pH of the suspension to 5.5 to 7.5 over a period of one to 10 hours, and baking the resulting scale-like inorganic particles coated with the zinc compound hydrolyzate at a temperature of 300° to 700° C., the obtained scale pigment coated with a zinc oxide has a high screening effect against ultraviolet rays including UV-A, shows good dispersibility in cosmetics when blended therein, and is capable of providing cosmetics which are excellent in tactile properties. The present invention has been achieved on the basis of this finding.

SUMMARY OF THE INVENTION

In the first aspect of the present invention, there is provided an ultraviolet-screening scale pigment comprising scale-like inorganic particles and a zinc oxide coating layer of 50 to 250 wt% (calculated as ZnO) based on the scale-like inorganic particles, a water content of the zinc oxide coating layer being not more than 7 wt%, and the pigment being obtained by preparing a suspension of the scale-like inorganic particles containing a water-soluble zinc compound, hydrolyzing the water-soluble zinc compound by lowering the pH of the suspension from a range of 9-11 to a range of 5.5-7.5 over a period of one to 10 hours and baking the obtained scale-like inorganic particles coated with a zinc compound hydrolyzate.

In the second aspect of the present invention, there is provided an ultraviolet-screening scale pigment comprising scale-like inorganic particles, a titanium oxide coating layer and a zinc oxide outer coating layer formed thereon, the amount of the zinc oxide coating layer being 50 to 250 wt% (calculated as ZnO) based on the scale-like inorganic particles, the pigment being obtained by preparing a suspension of the titanium oxide-coating scale-like inorganic particles containing a water-soluble zinc compound, hydrolyzing the water-soluble zinc compound while maintaining the pH of the suspension at 7.5 to 10 and baking the obtained titanium oxide-coating scale-like inorganic particles coated with a zinc compound hydrolyzate.

In the third aspect of the present invention, there is provided a process for preparing an ultraviolet-screening scale pigment, comprising the steps of adding to a suspension of scale-like inorganic particles an aqueous solution of a water-soluble zinc compound in an amount of 50 to 250 wt% (calculated as ZnO) based on the scale-like inorganic particles; adjusting pH of the suspension to a range of 9 to 11; hydrolyzing the water-soluble zinc compound while lowering the pH of the suspension to a range of 5.5 to 7.5 over a period of one to 10 hours; and baking the resulting scale-like inorganic particles coated with the zinc compound hydrolyzate at a temperature of 300° to 700° C. to convert the zinc compound hydrolyzate into a zinc oxide.

In the forth aspect of the present invention, there is provided a process for preparing an ultraviolet-screening scale pigment, comprising the steps of suspending scale-like inorganic particles in water, adding thereto an aqueous solution of a water-soluble titanium salt; maintaining the resulting suspension at a temperature between 90° C. and the boiling point so as to cause a hydrolytic reaction, thereby coating the surfaces of the scale-like inorganic particles with the titanium compound hydrolyzate; baking the resulting particles at a temperature of 500° to 900° C. to obtain the scale-like inorganic particles coated with titanium oxide; suspending these particles in water; heating the suspension to a temperature of 60° to 90° C.; adding thereto an aqueous solution of a water-soluble zinc compound in an amount of 50 to 250 wt% (calculated as ZnO) based on the scale-like inorganic particles while maintaining the pH of the suspension at a range of 7.5 to 10 to cause hydrolysis of the water-soluble zinc compound; and baking the resulting scale-like inorganic particles coated with the zinc compound hydrolyzate at a temperature of 300° to 700° C. to convert the zinc compound hydrolyzate into a zinc oxide.

In the fifth aspect of the present invention, there are provided cosmetics containing 0.1 to 60 wt% of the scale pigment as defined in the first aspect or the second aspect of the present invention.

DETAILED DESCRIPTION OF THE INVENTION

Figure 1:
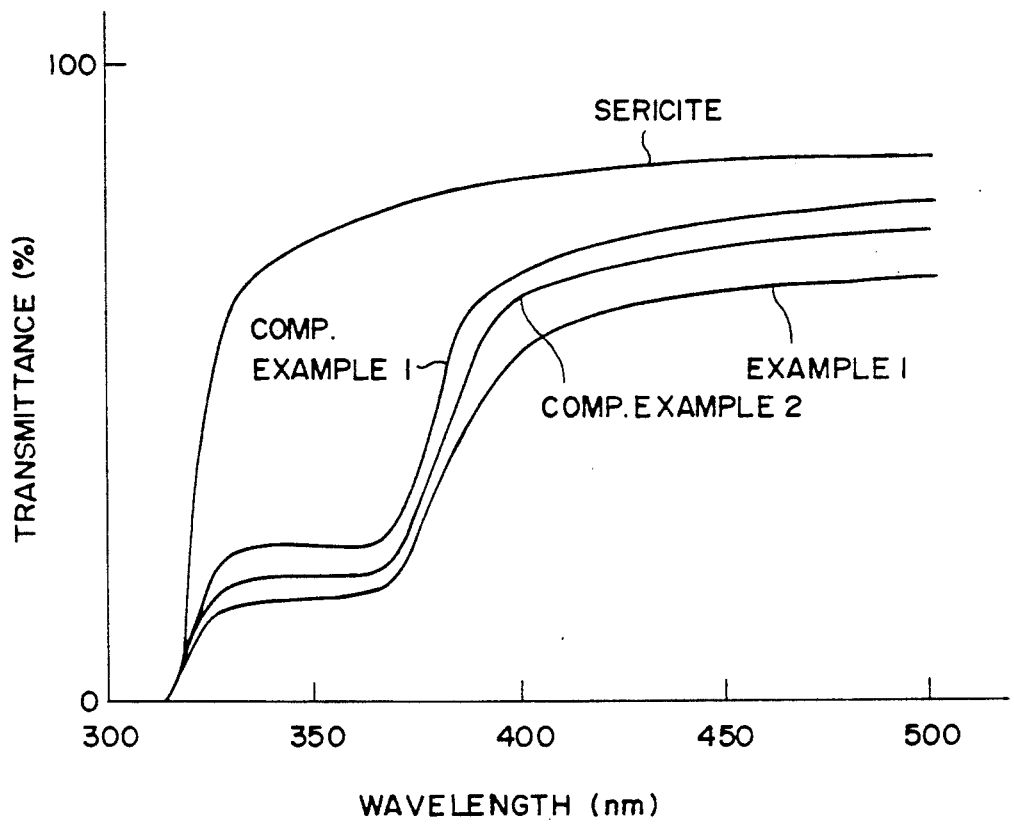
FIG. 1 is a graph showing transmittance of ultraviolet rays with wavelengths of 300 to 500 nm through the dispersed pastes containing the scale pigments of Example 1, Comparative Example 1 and Comparative Example 2 and sericite.

In the present invention, the "zinc oxide" used for coating the particle-surfaces of the scale-like inorganic particles means either zinc oxide or hydrous zinc oxide, and the "zinc compound hydrolyzate" means zinc hydroxide or hydrous zinc hydroxide. The zinc compound hydrolyzate is converted into a zinc oxide by baking, and the zinc oxide becomes hydrous zinc oxide or anhydrous zinc oxide depending on the temperature and time of the baking. The hydrous zinc oxide before baking and that after baking differ in water content. The water content of the hydrous zinc oxide in the present invention after baking is not more than about 7 wt%, which is far less than that (about 22 wt%) of the hydrous zinc oxide before baking.

In the present invention, scale-like inorganic particles used as a substrate have excellent dispersibility and can produce the cosmetics which are superior in dispersibility and tactile properties to those using a pigment composed of fine metallic oxide particles alone. The zinc oxide coated on the surfaces of the scale-like inorganic particles in the present invention has an excellent screening effect against ultraviolet rays including UV-A. Therefore, the zinc oxide-coating scale-like inorganic particles according to the present invention are useful as a pigment which has good dispersibility in cosmetic compositions, are excellent in tactile properties and show a high screening effect against ultraviolet rays including UV-A.

As the scale-like inorganic particles, there can be used particles of scale-like natural minerals such as mica, sericite, talc, kaolin, mullite, and scale-like synthetics such as synthetic mica.

The scale-like inorganic particles used in the present invention have an average particle size (average plate diameter of the scale-like particle) of usually 1 to 50 $\mu$m, preferably 5 to 30 $\mu$m, and an aspect ratio (ratio of average particle size (diameter) to plate thickness) of usually from 5 to 100, preferably from 20 to 70. The ratio of the major plate diameter to the minor plate diameter in the scale-like particle is usually 1:1 to 3:1. Preferably, the ratio of the major plate diameter to the plate thickness is from 8 to 150, and the ratio of the minor plate diameter to the plate thickness is from 2 to 50.

If the average particle size of the scale-like inorganic particles is greater than 50 $\mu$m, the particles when blended in a cosmetic composition, tend to give a feel of roughness and the prepared cosmetics tend to deteriorate in feel.

On the other hand, if the average particle size of the scale-like inorganic particles is less than 1 $\mu$m, the particles tend to be poor in dispersibility when blended in a cosmetic composition.

The amount of zinc oxide is 50 to 250 wt%, preferably 75 to 150 wt% (calculated as ZnO) based on the scale-like inorganic particles used as a substrate. If the coating amount of zinc oxide is less than 50 wt% (calculated as ZnO) based on the inorganic particles, it is difficult to obtain a satisfactory ultraviolet screening effect, and if the coating amount exceeds 250 wt%, the produced cosmetics may be deteriorated in feel on use.

The thickness of the coating layer on the scale-like inorganic particles is usually 50 to 200 nm, preferably 60 to 150 nm. The surfaces of the scale-like inorganic particles are uniformly coated with the zinc oxide.

An exposing ratio of the zinc atoms in the coating layer on the particle surfaces of the scale pigment, as determined by X-ray photoelectron spectroscopy, is usually not less than 50 atom%, preferably not less than 55 atom%, more preferably not less than 60 atom% based on the whole atoms exclusive of oxygen exposed on the particle surfaces.

The method of coating with zinc oxide in a preferred embodiment of the present invention comprises adding to a suspension of scale-like inorganic particles an aqueous solution of a water-soluble zinc compound in an amount of 50 to 250 wt%, preferably 75 to 150 wt% (calculated as ZnO) based on the scale-like inorganic particles, adjusting the pH of the resulting suspension to a range of 9 to 11, preferably 9.5 to 10.5, hydrolyzing the water-soluble zinc compound, usually at a temperature of 10° to 60° C., while lowering the pH of the suspension to a range of 5.5 to 7.5 over a period of one to 10 hours, preferably 4 to 10 hours, and baking the resulting scale-like inorganic particles coated with the zinc compound hydrolyzate at a temperature of 300° to 700° C. to convert the zinc compound hydrolyzate into the zinc oxide.

In the above process, the amount of the scale-like inorganic particles to be suspended in water is preferably 40 to 300 g, more preferably 70 to 150 g, to one liter of water.

Examples of the water-soluble zinc compounds usable in the above process include zinc sulfate, zinc chloride, zinc acetate and zinc nitrate. The amount of the water-soluble zinc compound added is one so that a zinc oxide coating layer of 50 to 250 wt% (calculated as ZnO) based on the scale-like inorganic particles to be coated with zinc oxide is formed on the scale-like inorganic particles. Concretely, it is preferred that the amount thereof is 50 to 250 g to one liter of suspending water.

When an aqueous solution of a water-soluble zinc compound is added to the aqueous suspension of scale-like inorganic particles, a water-soluble salt(s) of metallic elements forming white metallic oxides, such as Al, Si, Ti, Zr, may be added simultaneously with or after addition of an aqueous solution of a water-soluble zinc compound. Addition of such a water-soluble salt can conduce to improvement of dispersibility, weathering and light resistance. The water-soluble salts are added singly or in combination in a total amount of not more than 150 wt% (calculated as oxide such as $Al_2O_3$, $TiO_2$, $SiO_2$, $ZrO_2$) based on the scale-like inorganic particles.

After the addition of an aqueous solution of a water-soluble zinc compound, the pH of the resultant suspension is adjusted to 9 to 11 with an aqueous alkaline or acidic solution as required for effecting uniform coating of the surfaces of the scale-like inorganic particles with the zinc compound hydrolyzate. If the pH of the suspension is lower than 9, zinc is not dissolved perfectly, making it hard to obtain a uniform coat, while if the pH is higher than 11, the aqueous alkaline solution is wasted, resulting in poor economy.

Lowering of pH is usually effected by addition of an acidic solution.

If the period of hydrolysis is less than one hour, it tends to be difficult to obtain a uniform coat. It is to be also noted that no extra effect is provided even when the period of hydrolysis is made longer than 10 hours.

As the acidic solution, there can be used an aqueous solution of sulfuric acid, hydrochloric acid, acetic acid or the like. As the alkali source of the alkaline solution, there can be used hydroxides of alkaline metals such as sodium and potassium, aqueous ammonia and amines as well as such materials which become an alkali source on heating, such as urea.

In case of using an aqueous ammonia as the alkaline solution to adjust the pH to 9 to 11, it is possible to reduce pH by volatilizing ammonia by maintaining boiling with heating.

It is an important factor in carrying out the hydrolysis to effect gradual reduction of pH spending one to 10 hours.

After the surfaces of scale-like inorganic particles have been coated with the zinc compound hydrolyzate by the hydrolysis, the suspension is filtered, washed, dried and baked in the usual ways. The product may be subjected to pulverization after drying or baking.

The scale-like inorganic particles coated with the zinc compound hydrolyzate is baked at a temperature of 300° to 700° C. If the baking temperature is less than 300° C., the ultraviolet screening effect of the produced zinc oxide becomes low, while if the baking temperature is higher than 700° C., the scale pigment may disintegrate or the particles may be fused together to cause deterioration of dispersibility or growth of the zinc oxide particles, resulting in an excessive reduction of ultraviolet screening effect. The baking time, although variable depending on baking temperature, is usually 0.5 to 5 hours, preferably 2 to 5 hours.

The particle surfaces of the obtained scale pigment may be treated as desired with silicone, a higher fatty acid or a metallic salt thereof. Such a treatment improves dispersibility and wettability for the cosmetic base.

The method of coating with zinc oxide according to another embodiment of the present invention comprises suspending in water scale-like inorganic particles coated with a titanium oxide, heating the suspension to a temperature of 60° to 90° C., adding thereto an aqueous solution of a water-soluble zinc compound in an amount of 50 to 250 wt% (calculated as ZnO) based on the scale-like inorganic particles, maintaining the pH of the suspension at 7.5 to 10 with an alkaline solution, if necessary, to hydrolyze the water-soluble zinc compound, and baking the scale-like inorganic particles coated with the zinc compound hydrolyzate at a temperature of 300° to 700° C. to convert the zinc compound hydrolyzate into zinc oxide.

The scale-like inorganic particles coated with titanium oxide can be produced by the known methods. For example, it can be produced by a process which comprises suspending scale-like inorganic particles in water, adding thereto an aqueous solution of a water-soluble titanium salt such as titanyl sulfate, titanyl chloride, maintaining the pH of the resulting suspension at usually 0.5 to 2.5, preferably 1.0 to 2.0 and the temperature of the suspension between 90° C. and its boiling point, preferably between 95° C. and the boiling point (the boiling point being usually 100°–103° C.) to cause a hydrolytic reaction, thereby coating the particle surfaces of the scale-like inorganic particles with the hydrolyzate of titanium compound, and baking the obtained particles at a temperature of 500° to 900° C., preferably 700° to 850° C., to convert the titanium compound hydrolyzate into titanium oxide. In the above process, the hydrolysis is preferably carried out slowly over a period of one to 5 hours, preferably 2 to 5 hours.

The baking of the titanium compound hydrolyzate is carried out at a temperature of 500° to 900° C. for the reason that at a temperature of less than 500° C., the produced titanium oxide tends to be low in ultraviolet screening effect, while at a temperature of more than 900° C., the particles of the scale pigment may be collapsed or fused together to cause deterioration of dispersibility and resulting in an excessive reduction of ultraviolet screening effect. The baking time, although variable depending on baking temperature, is usually 0.5 to 5 hours.

The coating amount of titanium oxide is preferably 10 to 150 wt% (calculated as $TiO_2$) based on the scale-like inorganic particles used as substrate. If the coating amount of titanium oxide is less than 10 wt% (calculated as $TiO_2$) based on the scale-like inorganic particles, there may not be obtained a satisfactory ultraviolet screening effect, and if the coating amount exceeds 150 wt%, the cosmetics prepared by using the scale pigment may be deteriorated in feel on use.

The alkaline solution and the water-soluble zinc compound used in the above-described second embodiment of the invention may be the same as used in the first embodiment described previously.

The amount of the titanium oxide-coating scale-like inorganic particles to be suspended in water is preferably 40 to 300 g, preferably 100 to 200 g, to one liter of water.

The adding rate of the aqueous solution of a water-soluble zinc compound, though variable depending on the amount of the scale-like inorganic particles coated with titanium oxide and the amount of the aqueous solution, is preferably 0.05 to 5 g/min (calculated on ZnO) per 1 m² of the particle surface area of the scale-like inorganic particles.

If the adding rate of the aqueous solution of a water-soluble zinc compound is more than 5 g/min, the particle surfaces of the titanium oxide-coating scale-like inorganic particles tend to be not uniformly coated with zinc compound hydrolyzate, and hence coating of the titanium oxide-coating scale-like inorganic particles with zinc oxide is not effected perfectly, making it hard to obtain the desired ultraviolet screening effect. If the adding rate is less than 0.05 g/min, although no problem arises in the matter of product quality, the production efficiency lowers to pose an economical problem.

If an aqueous solution of a water-soluble zinc compound is added into the water suspension of titanium oxide-coating scale-like inorganic particles, a water-soluble salt of a metallic element forming a white metallic oxide, such as Al, Si, Ti, Zr, may be added simultaneously with or after dropping of the aqueous solution of zinc compound.

After hydrolysis of the water-soluble zinc compound, the suspension is filtered, washed, dried and baked according to usual methods. The baked product may be pulverized if necessary.

Also, the particle surfaces of the prepared scale pigment may be treated with silicone, a higher fatty acid or a metallic salt thereof.

Baking temperature and time in the second embodiment of the invention may be the same as in the first embodiment.

The ultraviolet screening scale pigment according to the present invention has an excellent screening effect against ultraviolet rays, especially UV-A, more particularly the ultraviolet rays with long wavelengths around 360 nm, and is also excellent in dispersibility in cosmetics and tactile properties. For instance, when this scale pigment is blended in a cosmetic preparation and its ultraviolet screening action is measured, in case sericite is used as scale-like inorganic particles, transmittance of ultraviolet rays with a wavelength of 360 nm is lowered to not more than 25% of that observed with the cosmetics using non-coated sericite particles.

The cosmetic preparations according to the present invention contain the scale pigment of the present invention as ultraviolet screening agent in an amount of 0.1 to 60 wt%. The cosmetic preparations according to the present invention have excellent screening effect against UV-A, especially the ultraviolet rays with long wavelengths around 360 nm.

The cosmetic preparations of the present invention can be obtained by dispersing the scale pigment of the present invention in a usually used cosmetic base composed of an oil such as vegetable oil, animal oil, mineral oil, synthetic oil (olive oil, lanolin, liquid paraffin, squalane, silicone oil, etc.), isopropyl myristate, isostearyl alcohol, triethanolamine.

Dispersion can be effected by using an appropriate means such as homomixer, sand grinder, two-roll mill.

The cosmetic preparations of the present invention may contain the additive(s) used in the ordinary cosmetics, such as surfactant, perfume, antiseptic, hardening preventive agent, colorant. If necessary, they may also contain other pigment(s) (mica, titanium white, particulate titanium oxide, iron oxide, etc.).

EXAMPLES

The present invention will be described more particularly below by referring to the examples, which examples however should be deemed merely illustrative and are not to be construed as limiting the scope of the invention.

Example 1

One hundred (100) g of sericite particles having an average particle size of 5 μm and an aspect ratio of 6 were suspended in one liter of water. Then an aqueous solution prepared by dissolving 353 g of zinc sulfate heptahydrate in one liter of water was added to the suspension with stirring. After adjusting the pH of the mixed solution to 10 with ammonia water, 10 wt% sulfuric acid was added into the solution slowly over a period of 5 hours, making the final pH thereof 6.

In this way, the surfaces of the sericite particles were coated with the zinc compound hydrolyzate and the coated sericite particles were filtered, washed with water, dried, pulverized and baked at a temperature of 400° C. for 2 hours to convert the zinc compound hydrolyzate into zinc oxide. There was thus obtained 120 g of a scale (flake) pigment having its particle surfaces coated with zinc oxide.

The coating amount of zinc oxide on the scale (flake) pigment (calculated as ZnO) based on sericite was 100 wt%, and the coating thickness of zinc oxide as measured by electron microphotography was about 100 nm.

The results of analysis of the particle surfaces of the scale (flake) pigment by an X-ray photoelectron spectroscopic analyzer (ESCA-850M mfd. by Shimadzu Corp.) are shown in Table 1.

Examples 2 to 5

Scale pigments were obtained in the same way as Example 1 except that the amount of zinc sulfate and baking temperature were changed as shown in Table 1. The thickness of coat of each of the obtained scale pigments and the results of the X-ray photoelectron spectroscopy are also shown in Table 1.

Comparative Example 1

One hundred (100) g (100 wt%, calculated as ZnO, based on sericite) of zinc oxide having a specific surface area of 30 m²/g was dry-mixed with 100 g of sericite having an average particle size of 5 μm and an aspect ratio of 6, and the mixture was treated in an oscillating ball mill for 120 minutes. There was obtained a scale pigment composed of sericite having its particle surfaces dry-coated with zinc oxide having a specific surface area of 30 m²/g.

The coating thickness and the results of X-ray photoelectron spectroscopy are shown in Table 1.

Comparative Example 2

A scale pigment was obtained by coating the surfaces of sericite particles with the zinc compound hydrolyzate as in Example 1 but not baking in Example 1.

The coating thickness and the results of X-ray photoelectron spectroscopy are shown in Table 1.

Test Example 1 (Ultraviolet screening effect)

One (1) g of each of the scale pigments obtained in Example 1 and Comparative Examples 1 and 2 and 9 g of nitrocellulose lacquer (solid content: 20 wt%) were mixed by a paint conditioner for 20 minutes to uniformly disperse each sample pigment. Each of the obtained dispersed pastes was applied to a transparent film by a 3-mil applicator and transmittance of ultraviolet rays with wavelengths of 300 to 500 nm through each of the dispersed pastes was measured by using a spectrophotometer (model U-3410, mfd. by Hitachi Corp.). The results are shown in FIG. 1.

In FIG. 1, the wavelength of ultraviolet rays is plotted as abscissa and the transmittance as ordinate It will be noted that the lower the transmittance at a wavelength, the greater the screening effect at that wavelength.

In FIG. 1, each of the curves showing the relation between wavelength and transmittance for the respective dispersed pastes are marked with Example No. or Comparative Example No. to allow discrimination of the curves.

There was also prepared a dispersed paste in the same way as described above except that the scale pigment used in Example 1 or Comparative Example 1 or 2 was replaced with the same amount of sericite, and the result of measurement of ultraviolet transmittance through this paste was also shown in FIG. 1 (the curve indicated by "SERICITE").

As is seen from FIG. 1, the dispersed paste using the scale pigment of Example 1 was lower in ultraviolet transmittance than, and hence superior in ultraviolet screen effect to the dispersed pastes using the scale pigments of Comparative Examples 1 and 2 and sericite.

Also, the scale pigment of Example 1 had good dispersibility and was superior to the scale pigments of Comparative Examples 1 and 2 and sericite.

Example 6

Ninety (90) g of sericite having an average particle size of 5 $\mu$m and an aspect ratio of 6 was suspended in one liter of water. Then 35 g (calculated as $TiO_2$) of a 200 g/l aqueous solution of titanyl sulfate was added to the resultant suspension with stirring. Thereafter, the suspension was heated at a rate of 1° C./min, boiled for 4 hours to hydrolyze titanyl sulfate, then filtered and washed with water to obtain the sericite particles having their surfaces coated with the titanium compound hydrolyzate.

The thus obtained sericite particles coated with the titanium compound hydrolyzate were again suspended in water and their coating treatment was repeated under the same conditions as in the first coating operation. After 3 rounds of coating operation, the suspension was filtered, washed with water and dried. The resulting product was baked at a temperature of 850° C. for 2 hours to convert the titanium compound hydrolyzate into titanium oxide and then pulverized to obtain 163 g of titanium oxide-coating sericite.

The coating amount of titanium oxide was 100 wt% (calculated as $TiO_2$) based on sericite.

In one liter of water, 100 g of the titanium oxide-coating sericite was suspended, stirred and heated to a temperature of 80° C., and then an aqueous solution formed by dissolving 353 g of zinc sulfate heptahydrate in one liter of water was added dropwise to the suspension over a period of 90 minutes. During this operation, 0.1N sodium hydroxide solution was simultaneously added dropwise to the suspension to maintain the pH of the suspension at 9.0 to hydrolyze zinc sulfate.

In this way, the sericite particle surfaces coated with titanium oxide was further coated with the zinc compound hydrolyzate, and then the suspension was filtered, washed with water, dried, pulverized and baked at a temperature of 500° C. for 2 hours to convert the zinc compound hydrolyzate into zinc oxide to obtain 120 g of sericite having a titanium oxide coating layer and a zinc oxide coating layer thereon.

The coating amount of zinc oxide was 200 wt% (calculated as ZnO) based on sericite.

The zinc oxide-coating thickness as measured by electron microphotography was about 100 nm.

EXAMPLE 7

A scale pigment was obtained in the same way as Example 6 except that the amount of zinc sulfate was changed to 212 g. The thickness of the zinc oxide coating layer and the results of its X-ray photoelectron spectroscopy are shown in Table 1.

COMPARATIVE EXAMPLE 3

Ninety (90) g of sericite having an average particle size of 5 $\mu$m and an aspect ratio of 6 was suspended in one liter of water. Then 35 g (calculated as $TiO_2$) of a 200 g/l aqueous solution of titanyl sulfate (calculated as $TiO_2$) was added to the suspension with stirring. The suspension was then heated at a rate of 1° C./min., boiled for 4 hours to hydrolyze titanyl sulfate, then filtered and washed with water to obtain the sericite particles having their surfaces coated with the titanium compound hydrolyzate.

The thus obtained sericite particles coated with the titanium compound hydrolyzate were again suspended in water, and their coating treatment was repeated under the same conditions as in the first coating operation. After 3 rounds of the coating treatment, the suspension was filtered, washed with water, dried, baked at a temperature of 850° C. for 2 hours to turn the titanium compound hydrolyzate into titanium oxide and then pulverized to obtain 163 g of titanium oxide-coating sericite.

The coating amount of titanium oxide was 100 wt% (calculated as $TiO_2$) based on sericite.

The thickness of the coating layer and the results of its X-ray photoelectron spectroscopy are shown in Table 1.

COMPARATIVE EXAMPLE 4

One hundred (100) g of sericite having an average particle size of 5 $\mu$m and an aspect ratio of 6 was suspended in one liter of water, an the suspension was stirred and heated to a temperature of 80° C. Then an aqueous solution prepared by dissolving 353 g of zinc sulfate heptahydrate in one liter of water was added dropwise to the suspension over a period of 90 minutes. During this operation, 0.1N sodium hydroxide solution was simultaneously added dropwise to the suspension to maintain its pH at 9.0 to hydrolyze zinc sulfate.

In this way, the sericite particle surfaces were coated with the zinc compound hydrolyzate, and then the suspension was filtered, washed with water, dried, pulverized and baked at a temperature of 500° C. for 2 hours to convert the zinc compound hydrolyzate into zinc oxide. There was consequently obtained 120 g of zinc oxide-coating sericite.

The coating amount of zinc oxide was 100 wt% (calculated as ZnO) based on sericite. The zinc oxide-coating thickness as measured by electron microphotography was about 100 nm. The results of X-ray photoelectron spectroscopy of the coat are shown in Table 1.

Comparative Example 5

The procedure of Example 6 was followed for coating the sericite particle surfaces with titanium oxide and further coating the titanium oxide with the zinc compound hydrolyzate. However, unlike Example 6, the product was not baked.

The coating thickness and the results of X-ray photoelectric analysis of the coat are shown in Table 1.

Test Example 2

There were prepared the oil-type anti-suntan cosmetics having the following formulation by using the scale pigments obtained in Example 6 and Comparative Examples 3 to 5. Each of the prepared cosmetics was applied on a transparent film by a 3-mil applicator, and transmittance of ultraviolet rays with wavelengths of 300 to 500 nm through each of the cosmetics was measured by using a spectrophotometer model U-3410 (manufactured by Hitachi Corp.). The results are shown in FIG. 2.

| Formulation of anti-suntan cosmetics | |
| --- | --- |
| Scale pigment | 0.167 g |
| Nylon 12 | 0.333 g |
| Squalane | 45.0 g |
| Olive oil | 5.0 g |
| Isopropyl myristate | 49.5 g |

Figure 2:
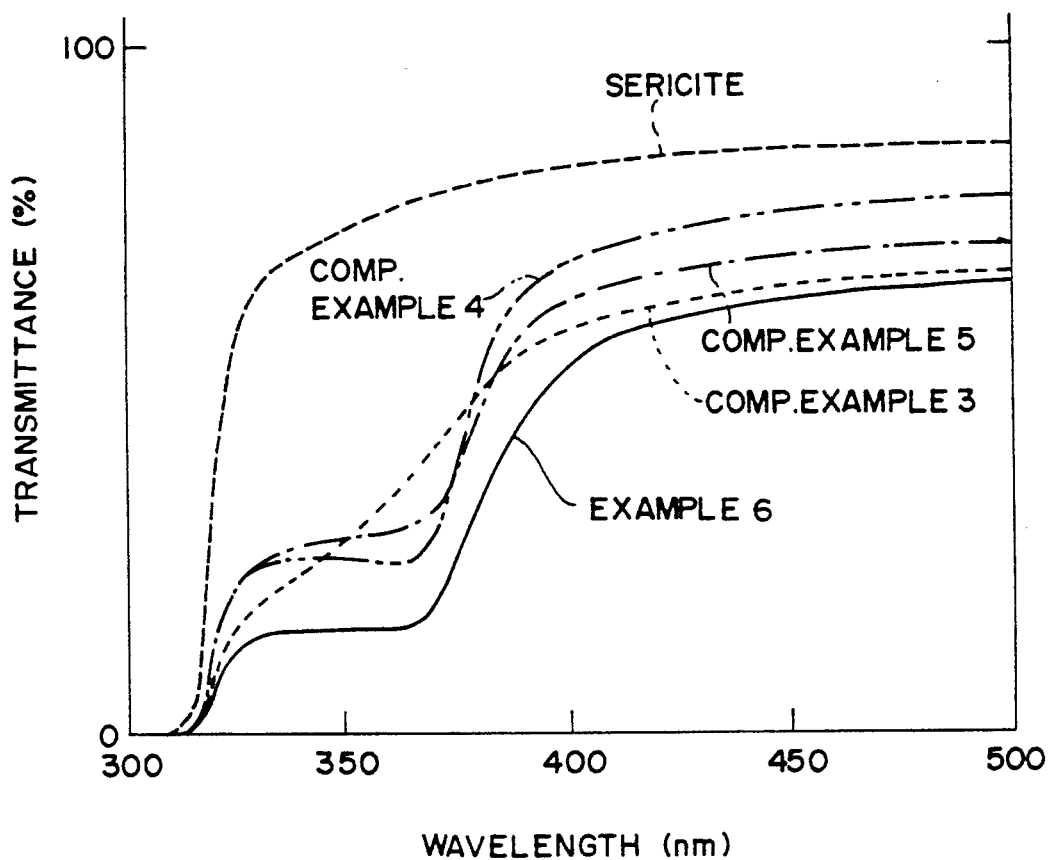
FIG. 2 is a graph showing transmittance of ultraviolet rays with wavelengths of 300 to 500 nm through the anti-suntan cosmetics containing the scale pigments of Example 6 and Comparative Examples 3 to 5 and sericite.

In FIG. 2, the wavelength of ultraviolet rays is plotted as abscissa and the transmittance as ordinate. The lower the transmittance at a wavelength, the greater the ultraviolet screening effect at that wavelength. Also in FIG. 2, the curves showing the relation between wavelength and transmittance for the respective cosmetics are marked with Example No. or Comparative Example No. of the scale pigment compositions used for the respective cosmetics to allow discrimination of the curves.

There was also prepared an anti-suntan cosmetic composition with the same formulation as shown above except that the scale pigment was replaced by the same amount of sericite, and the ultraviolet transmittance was measured for this cosmetic composition. The results are shown in Table 2.

As seen from FIG. 2, the cosmetic preparation using the scale pigment composition of Example 6 was lower in transmittance, and hence higher in ultraviolet screening effect, than the cosmetic preparations using the scale pigment compositions of Comparative Examples 3-5 and sericite.

The cosmetic preparation using the scale pigment composition of Example 6 was also low in transmittance of UV-A with wavelengths of 320 to 400 nm, indicating its excellent screening effect against UV-A.

Further, the scale pigment composition of Example 6 showed good dispersibility in preparation of the antisuntan cosmetics, and no inferiority of dispersibility was noted in comparison with the scale pigment compositions of Comparative Examples 3-5 and sericite.

Test Example 3 (Evaluation of tactile property)

For evaluation of tactile property (feel on application to the skin), there was prepared the samples of anti-suntan solid foundation having the following composition:

| | |
| --- | --- |
| Scale pigment or sericite | 45.0 wt % |
| Talc | 35.0 wt % |
| Titanium dioxide pigment | 10.0 wt % |
| Iron oxide pigment (red) | 1.4 wt % |
| Iron oxide pigment (black) | 0.2 wt % |
| Iron oxide pigment (yellow) | 2.9 wt % |
| Isostearyl alcohol | 2.0 wt % |
| Lanolin | 2.0 wt % |
| Sorbitan fatty acid ester | 0.5 wt % |
| Triethanolamine | 1.0 wt % |
| Perfume | proper amount |

Lanolin, sorbitan fatty acid ester, triethanolamine and perfume was previously mixed by heating at a temperature of 70° C. and the resultant mixture was added to a mixture of the remaining particle materials, and after sufficient mixing, the whole mixture was press molded to obtain anti-suntan solid foundation.

Each of the obtained samples of solid foundation was applied to the skin of a panel of 10 persons and it is evaluated feel on application to the skin of the samples of foundation from the aspects of spreading and adhesive qualities.

The criterion for evaluation is as follows. The figures in Table 2 are each the average of the values given by the panel.

| Criterion for evaluation |
| --- |
| 4: Very good |
| 3: Good |
| 2: Ordinary |
| 1: Poor |

As apparent from the results shown in Table 2, the solid foundation using the scale pigment of Examples 1 to 7 was higher in rating of both spreading and adhesive qualities, and hence better in feel, than the solid foundations using the scale pigments of Comparative Examples 1 to 5. Also, the former was same in the rating as the solid foundation using sericite (Reference example), and no deterioration of feel due to coating with zinc oxide was observed. The ratings of not less than 3.5 in both the qualities are practically acceptable.

Test Example 4

Organoleptic evaluation was made according to the following criterion, with a panel of 5 persons being asked to actually rub the pigment against the skin and evaluate the feel of the pigment to the skin.

| Standard material | Rating |
| --- | --- |
| Non-treated sericite (average particle size: 30 μm) | 5 |
| 15% TiO$_2$-coating sericite (% based on sericite; average particle size: 30 μm) | 3 |
| 50% TiO$_2$-coating sericite (% based on sericite; average particle size: 30 μm) | 1 |

The results are shown in Table 2. The rating of not less than 3.5 is practically acceptable.

TABLE 1

| | Scale-like inorganic particles (substrate) (g) | TiO₂ coating (g) | Zinc sulfate heptahydrate (g) | Baking temp. after coating (°C.) | Coated ZnO (wt % based on the substrate) | ZnO Coating thickness (nm) | Zn | Si | Al | K | Ti |
|---|---|---|---|---|---|---|---|---|---|---|---|
| | | | | | | | \multicolumn{5}{c}{Ratios of the elements in the surface (atom %)} |

| | Scale-like inorganic particles (substrate) (g) | TiO₂ coating (g) | Zinc sulfate heptahydrate (g) | Baking temp. after coating (°C.) | Coated ZnO (wt % based on the substrate) | ZnO Coating thickness (nm) | Zn | Si | Al | K | Ti |
|---|---|---|---|---|---|---|---|---|---|---|---|
| Example 1 | Sericite (100) | No Coating | 353 | 400 | 100 | 100 | 67 | 23 | 8 | 2 | — |
| Example 2 | Sericite (100) | No Coating | 716 | 400 | 203 | 170 | 87 | 13 | 0 | 0 | — |
| Example 3 | Sericite (100) | No Coating | 187 | 400 | 53 | 58 | 57 | 26 | 13 | 4 | — |
| Example 4 | Sericite (100) | No Coating | 353 | 500 | 100 | 92 | 70 | 20 | 4 | 2 | — |
| Example 5 | Sericite (100) | No Coating | 353 | 600 | 100 | 83 | 72 | 18 | 4 | 2 | — |
| Example 6 | Sericite (50) | Coated (50) | 353 | 500 | 200 | 100 | 77 | 15 | 0 | 0 | 8 |
| Example 7 | Sericite (50) | Coated (50) | 212 | 500 | 120 | 63 | 53 | 17 | 8 | 3 | 19 |
| Comp. Example 1 | Sericite (100) | No Coating | Zinc oxide 100 (dry-coating) | No baking | 100 | —*1 | 25 | 50 | 19 | 6 | — |
| Comp. Example 2 | Sericite (100) | No Coating | 353 | No baking | 100 | 100 | 37 | 43 | 15 | 5 | — |
| Comp. Example 3 | Sericite (50) | Coated (50) | 0 | No baking | — | — | — | 23 | 10 | 4 | 63 |
| Comp. Example 4 | Sericite (100) | No Coating | 353 | 500 | 100 | 100 | 45 | 34 | 15 | 6 | — |
| Comp. Example 5 | Sericite (50) | Coated (50) | 353 | No baking | 106 | 100 | 40 | 30 | 13 | 7 | 10 |
| Reference Example | Sericite | — | — | — | — | — | — | 48 | 42 | 10 | — |

Note:
*1: not uniformly coated

TABLE 2

| | Trans- mittance at 360 (nm) | Feel of pigment to skin | | Test example 4 |
|---|---|---|---|---|
| | | Test example 3 | | |
| | | Spreading quality | Adhesive quality | |
| Example 1 | 17 | 4.0 | 4.0 | 4.0 |
| Example 2 | 8 | 3.8 | 3.8 | 4.0 |
| Example 3 | 25 | 4.6 | 4.6 | 4.4 |
| Example 4 | 18 | 4.0 | 4.0 | 4.2 |
| Example 5 | 18 | 4.0 | 4.0 | 4.2 |
| Example 6 | 15 | 4.0 | 4.0 | 4.2 |
| Example 7 | 20 | 4.4 | 4.6 | 4.6 |
| Comp. Example 1 | 25 | 1.9 | 2.8 | 2.4 |
| Comp. Example 2 | 20 | 2.9 | 3.1 | 2.6 |
| Comp. Example 3 | 33 | 1.8 | 1.5 | 1 |
| Comp. Example 4 | 29 | 2.9 | 2.1 | 2.2 |
| Comp. Example 5 | 25 | 1.9 | 1.6 | 2.2 |
| Reference example | 76 | 4.0 | 4.0 | 5 |

Examples 8 to 10

There were prepared an anti-suntan emulsion (Example 8), anti-suntan particles (Example 9) and sunscreen compact (Example 10) having the following compositions by using the scale pigment obtained in Example 1 or Example 6.

| | Parts by weight |
|---|---|
| Anti-suntan emulsion | |
| Scale pigment (Example 1) | 0.167 |
| Nylon 12 | 0.333 |
| Squalane | 45.0 |
| Olive oil | 5.0 |
| Isopropyl myristate | 49.5 |
| Anti-suntan powder | |
| Scale pigment (Example 1) | 55.0 |
| Crystalline cellulose | 10.0 |
| Ultramarine | 1.0 |
| Spherical calcium silicate | 14.0 |
| Squalane | 20.0 |

(The above materials were mixed by a Henschel mixer and the mixture was made into powder.)

| | Parts by weight |
|---|---|
| Sunscreen compact | |
| Scale pigment (Example 6) | 50.0 |
| Fine titanium oxide particles | 23.0 |
| Red iron oxide | 0.2 |
| Ultramarine | 0.04 |
| Yellow iron oxide | 0.4 |
| Milk powder | 2.0 |
| Sericite | 10.0 |
| Aluminum stearate | 2.0 |
| Mica | 10.0 |
| Silicic acid ester | 3.3 |

What is claimed is:

1. An ultraviolet-screening scale pigment comprising scaly inorganic particles and a zinc oxide coating layer of 50 to 250 wt% (calculated as ZnO) based on the scaly inorganic particles, the ratio of zinc exposed on the surfaces of the pigment particles, as measured by X-ray photoelectron spectroscopy, being not less than 50 atom% based on all atoms exclusive of oxygen exposed on the surfaces of the pigment particles, and obtained by preparing a suspension of the scaly inorganic particles containing a water-soluble zinc compound, hydrolyzing the water-soluble zinc compound by lowering the pH of the resultant suspension from a range of 9 to 11 to a range of 5.5 to 7.5 over a period of 1 to 10 hours and baking the obtained scaly inorganic particles coated with the zinc compound hydrolyzate, the water content of said zinc oxide coating layer being not more than 7 wt%.

2. A scale pigment according to claim 1, wherein the scaly inorganic particles are selected from the group consisting of particles of mica, sericite, talc, kaolin, mullite and synthetic mica.

3. A scale pigment according to claim 1, wherein the scaly inorganic particles have an average particle size of 1 to 50 μm and an aspect ratio of 5 to 100.

4. A scale pigment according to claim 1, wherein a thickness of the zinc oxide coating layer is 50 to 200 nm.

5. A scale pigment according to claim 1, wherein the scaly inorganic particles are sericite particles, and a transmittance of ultraviolet rays with a wavelength of 360 nm through said ultraviolet-screening scale pigment is not more than 25% based on the transmittance of said ultraviolet rays through non-coated sericite particles.

6. An ultraviolet-screening scale pigment comprising scaly inorganic particles coated with titanium oxide and a zinc oxide outer coating layer formed thereon of 50 to 250 wt% (calculated as ZnO) based on the scaly inorganic particles, the ratio of zinc exposed on the surfaces of the pigment particles, as measured by X-ray photoelectron spectroscopy, is not less than 50 atom% based on all atoms exclusive of oxygen exposed on the surfaces of the pigment particles, and obtained by preparing a suspension of the titanium oxide-coating scaly inorganic particles containing a water-soluble zinc compound, hydrolyzing the water-soluble zinc compound while maintaining the pH of the suspension at 7.5 to 10 and baking the obtained titanium oxide-coating scaly inorganic particles coated with the zinc compound hydrolyzate.

7. A scale pigment according to claim 6, wherein an amount of the titanium oxide coating layer is 10 to 150 wt% (calculated as $TiO_2$) based on the scaly inorganic particles.

8. A scale pigment according to claim 6, wherein the scaly inorganic particles are selected from the group consisting of particles of mica, sericite, talc, kaolin, mullite and synthetic mica.

9. A scale pigment according to claim 6, wherein the scaly inorganic particles have an average particle size of 1 to 50 μm and an aspect ratio of 5 to 100.

10. A scale pigment according to claim 6, wherein a thickness of the zinc oxide coating layer is 50 to 200 nm.

11. A scale pigment according to claim 6, wherein the scaly inorganic particles are sericite particles, and the transmittance of ultraviolet rays with a wavelength of 360 nm through said ultraviolet-screening scale pigment is not more than 25% based on the transmittance of said ultraviolet rays through non-coated sericite particles.

12. A process for preparing an ultraviolet-screening scale pigment, comprising the steps of
adding to a suspension of scaly inorganic particles an aqueous solution of a water-soluble zinc compound in an amount of 50 to 250 wt% (calculated as ZnO) based on said scaly inorganic particles,
adjusting pH of the suspension to a range of 9 to 11,
hydrolyzing the water-soluble zinc compound while lowering the pH of the suspension to a range of 5.5 to 7.5 over a period of one to 10 hours, and
baking the resulting scaly inorganic particles coated with the zinc compound hydrolyzate at a temperature of 300° to 700° C. to convert the zinc hydrolyzate into a zinc oxide.

13. A process according to claim 12, wherein said hydrolysis is carried out by adding an aqueous acidic solution to the suspension.

14. A process according to claim 12, wherein an aqueous ammonia is added to the suspension composed of the scaly inorganic particles and the water-soluble zinc compound to adjust the pH of the suspension to a range of 9 to 11, and the hydrolysis is carried out by volatilizing ammonia with heating.

15. A process according to claim 12, wherein an amount of scaly inorganic particles in the suspension is 40 to 300 g per 1,000 ml of water.

16. A process according to claim 12, wherein the water-soluble zinc compound is selected from the group consisting of zinc sulfate, zinc chloride, zinc acetate and zinc nitrate.

17. A process for preparing an ultraviolet-screening scale pigment, comprising the steps of
suspending scaly inorganic particles in water,
adding thereto an aqueous solution of a water-soluble titanium salt,
maintaining the resulting suspension at a temperature between 90° C. and the boiling point to cause a hydrolytic reaction, thereby coating the surfaces of the scaly inorganic particles with the titanium compound hydrolyzate,
baking the resulting particles at a temperature of 500° to 900° C. to form the scaly inorganic particles coated with a titanium oxide,
suspending these particles in water,
heating the suspension to a temperature of 60° to 90° C.,
adding thereto an aqueous solution of a water-soluble zinc compound in an amount of 50 to 250 wt% (calculated as ZnO) based on said scaly inorganic particles while maintaining the pH of the suspension at a range of 7.5 to 10, thereby arising hydrolysis of said water-soluble zinc compound, and
baking the resulting scaly inorganic particles coated with the zinc compound hydrolyzate at a temperature of 300° to 700° C. to convert the zinc compound hydrolyzate into a zinc oxide.

18. The process according to claim 17, wherein an amount of scaly inorganic particles coated with titanium oxide in the suspension is 40 to 300 g per 1,000 ml of water.

19. The process according to claim 17, wherein the water-soluble zinc compound is selected from the group consisting of zinc sulfate, zinc chloride, zinc acetate and zinc nitrate.

20. The process according to claim 17, wherein an adding rate of the aqueous solution of the water-soluble zinc compound is 0.05 to 5 g/min (calculated as ZnO) per 1 m² of surface area of the scaly inorganic particles.

21. Cosmetics containing 0.1 to 60 wt% of the scale pigment as defined in claim 1.

22. Cosmetics containing 0.1 to 60 wt% of the scale pigment as defined in claim 6.

* * * * *